United States Patent [19]
Cohen et al.

[11] 3,949,477
[45] Apr. 13, 1976

[54] ORTHODONTIC METHOD AND APPARATUS

[76] Inventors: Morton Cohen, Fox Pavilion, Suite 604, Jenkintown, Pa.; Elliott Silverman, 4829 Atlantic Ave., Ventnor, N.J.

[22] Filed: Nov. 18, 1974

[21] Appl. No.: 524,470

[52] U.S. Cl. .............................................. 32/14 A
[51] Int. Cl.² .......................................... A61C 7/00
[58] Field of Search ...... 32/14 A, 14 B, 14 R, 14 C, 32/14 E

[56] References Cited
UNITED STATES PATENTS
3,452,436  7/1969  De Woskin ......................... 32/14 A
3,738,005  6/1973  Cohen et al. ........................ 32/14 B
3,745,653  7/1973  Cohl ................................... 32/14 A Primary Examiner—Louis G. Mancene
Assistant Examiner—Jack Q. Lever

[57] ABSTRACT

In the application of orthodontic brackets to teeth by the indirect method employeing a transfer tray, the use of adhesive activating radiant energy passing through the transfer tray or mold and apparatus for conducting the radiant energy from the mold or exteriorly thereof, through the latter to the bracket adhesive to be activated.

13 Claims, 7 Drawing Figures

ORTHODONTIC METHOD AND APPARATUS

BACKGROUND OF THE INVENTION

The present invention constitutes an improvement over the invention of our prior patent U.S. Pat. No. 3,738,005, wherein adhesive curing was not accurately controllable as to occurrence, both commencement and duration of adhesive curing being inherent in the method rather than selectively controllable. This lack of accurate control of the adhesive required relatively high skill of the practitioner.

SUMMARY OF THE INVENTION

It is an important object of the present invention to provide an orthodontic method and apparatus for applying brackets to teeth which is highly simplified so as to require relatively little skill of the practitioner, while being assured of highly accurate results.

It is a further object of the present invention to provide a unique method and apparatus for applying orthodontic brackets which is extremely quick, sure and highly reliable so as to save considerable time to both patient and practitioner, without sacrificing quality of work and results.

Other objects of the present invention will become apparent upon reading the following specification and referring to the accompanying drawings, which form a material part of this disclosure.

The invention accordingly consists in the features of construction, combination and arrangements of parts and method steps, which will be exemplified in the following description, and of which the scope will be indicated by the appended claims.

DESCRIPTION OF THE PREFERRED EMBODIMENT

Figure 1:
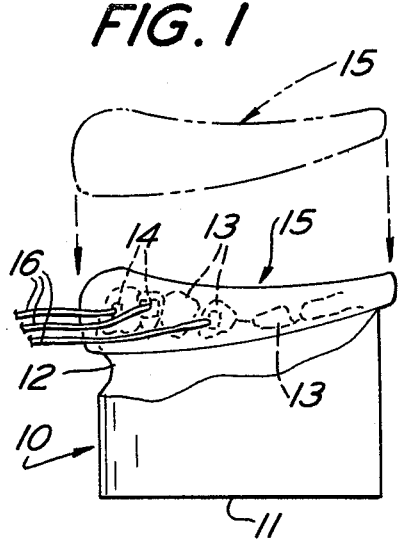
FIG. 1 is a side elevational view showing a dental cast and a positioner, mold or tray having been applied to the dental cast, the positioner being shown in phantom apart from the dental cast.
Figure 2:
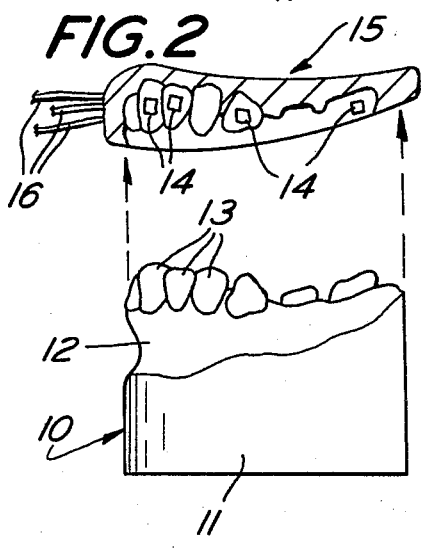
FIG. 2 is an elevational view similar to FIG. 1, showing the dental cast and positioner, the latter being shown partially in section as having been removed from the dental cast.

Referring now more particularly to the drawings, and specifically to FIG. 1 thereof, a dental cast is there generally designated 10, which of itself may be conventional, being formed of plaster to accurately simulate the gums and teeth of a patient. The dental cast 10 includes a base part 11, a gum simulating region 12 extending from the base, and simulated teeth 13 projecting from the gum simulating region 12. Thus, the simulated teeth 13 and gum region 12 are an accurate model of the patient.

With the dental cast 10, the orthodontist may determine the optimum locations and arrangements of dental brackets. That is, the orthodontist may choose the proper type of bracket and select an optimal location and arrangement on the teeth. It will be seen that certain of the teeth 13 carry brackets 14, the latter being selectively positioned on the teeth. The brackets 14 on the teeth 13 of the dental cast 10 are detachably or removably positioned, as by wax, a tacky adhesive or other suitable means.

With the brackets 14 selectively positioned and detachably secured to the dental cast teeth 13, a quantity of molding material in a plastic condition is conformably applied to the teeth 13, brackets 14 and adjacent portions of the gum simulating region 12. The molding material may be of any suitable type, and it has been found satisfactory to employ thermoplastic material in a heated or plastic condition for convenient moldability into conforming engagement with the cast teeth 13, brackets 14 and adjacent portions of the gum region 12. The molded material is shown in solid lines in FIG. 1 as a mold, positioner or tray 15, which is of a flexible, self-sustaining, resilient character and has been molded into positive, capturing engagement with the brackets 14. For example, the material of mold 15 extends into undercuts of the brackets 14 so as to capture and releasably retain the latter.

In addition, there are provided one or more radiant energy conductors 16 extending from the exterior of mold 15 inwardly therethrough, being embedded therein, and each terminating adjacent to a respective bracket 14. The conductors 16 may be of glass or fiber-optic type for conducting light, metal for conducting heat, or other suitable radiant energy conductive material. In practice, the conduction of light, and particularly light in the ultraviolet range, has been found advantageous, for reasons which will appear presently. Exteriorly of the mold, tray or positioner 15, the radiant energy conductors 16 may be connected to a source of radiant energy, such as a source 17, see FIG. 3 which may be an ultraviolet light source, heat source, ultrasonic sound source, or other. The radiant energy source 17 may be provided with an actuating means or switch 18, and a supply cord 19 for connection to a power source.

Upon withdrawal of the mold 15 from the dental cast 10, as from the solid line position of FIG. 1 to the phantom position thereof, the brackets 14 are removed from the dental cast teeth 13 by the positive action of the mold. That is, the brackets 14 are retained by the mold 15 upon its removal from the dental cast 10, the temporary retaining means employed to position the brackets being insufficient to retain the brackets against the positive withdrawing force of the mold 15. The mold 15 is shown in detail in FIG. 3, where it will be observed that the mold has captured interiorly thereof the brackets 14, the latter being releasably but positively retained in position within the mold by engagement of the mold material in undercuts of the bracket. The several radiant energy conductors 16 each extend through the mold 15 to terminate at a respective bracket 14, for purposes appearing more fully hereinafter.

Figure 3:
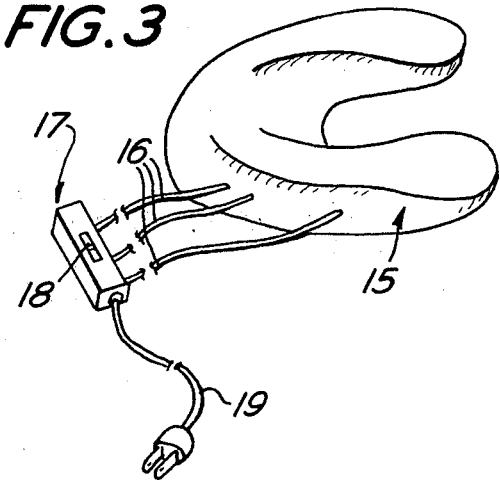
FIG. 3 is a top perspective view showing the positioner, mold or tray apart from the dental cast.
Figure 4:
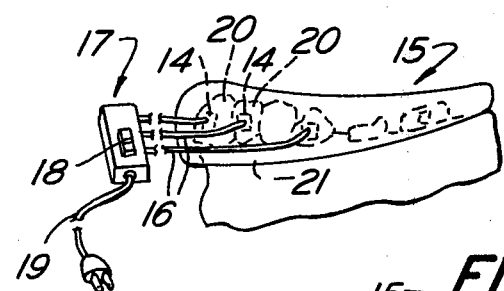
FIG. 4 is a partial side elevational view showing the positioner of FIGS. 3 and 2, as applied to a patient's teeth.

As shown in FIG. 3, the mold 15 apart from the dental cast 10 transports the captured brackets, and positions the latter properly on the patient's teeth, as shown in FIG. 4.

Before actual location of the mold 15 in conforming engagement with the patient's teeth 20 and adjacent gum portion 21 of the patient, the teeth are dried, or otherwise prepared to receive a chemical adhesive or component thereof, placed on either or both of the brackets 14 and patient's teeth 20. In practice, a sealant has been placed on the patient's teeth, such as the adhesive sealant sold under the trademark Nuva Seal by Dentsply Corp., which sealant is sensitive to ultraviolet light and may or may not be polymerized at this stage, as desired. The contact surfaces of the brackets 14 captured within the mold or tray 15 may have applied thereto a chemical adhesive, such as Nuva Tach, an adhesive cooperable with Nuva Seal to cure in response to activation by ultraviolet light. The product Nuva Tach is also an adhesive product of Dentsply Corp. However, other remotely activatable adhesive systems may be employed, as desired.

The tray or mold 15, with the bracket contact surfaces having an adhesive material applied thereto, is placed in position on the patient's teeth which automatically and simultaneously properly locates all of the brackets, each in facing relation with a respective tooth, and the mold, positioner or tray is in conforming engagement with the teeth and gums.

Curing or setting of the adhesive is then occasioned at a selected point in time by actuation of the activator 17, which may be an ultraviolet light source transmitting ultraviolet radiation through conductors 16 to respective brackets 14 for curing the adhesive interposed between the associated bracket and adjacent tooth. The conductors 16 may terminate at a position contiguous to and along side of a respective bracket 14 for transmitting radiant energy to the adhesive material, or the brackets may be permeable to the radiant energy, as by transparency or perforations.

As selectively activatable material cures or sets faster and the commencement of curing is selected by the operator, it will be understood that precision of bracket location is assured with a minimum of difficulty, even when performing upon youngsters.

Figure 5:
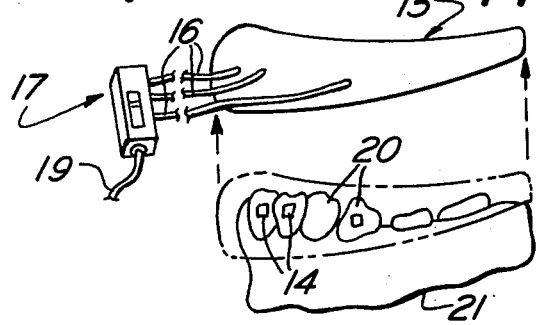
FIG. 5 is an elevational view similar to FIG. 4, but illustrating the positioner having been removed from the patient's teeth while the orthodontic brackets remain positioned on the teeth.

After curing or setting of the adhesive to securely fasten brackets 14 to the patient's teeth 20, the positioner, mold or tray is withdrawn or removed from the conforming engagement of FIG. 4, as in the direction of arrows in FIG. 5. The positioner, mold or tray 15 may be suitably flexed, as required, to release the brackets, which are now fixedly secured in their precise selected positions on their respective teeth, as shown in FIG. 5. Necessary wiring and other orthodontic procedures may now be performed.

Figure 6:
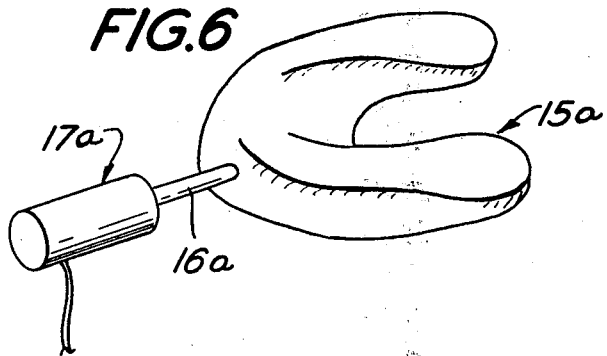
FIG. 6 is a top perspective view showing a positioner, mold or tray of the present invention including a slightly modified embodiment of adhesive activating means.

Referring now to the embodiment of FIG. 6, it will there be seen that a mold, tray or positioner 15a is provided which may be generally identical to the tray 15. However, the radiant energy source 17a may assume the configuration of a gun, being provided with a probe 16a for conducting radiant energy. The probe 16a may be inserted into the mold or tray 15a for conduction of radiant energy through the mold to each bracket and its associated adhesive.

Also in the embodiment of FIG. 6, the mold 15a may be transparent or permeable to the radiant energy, whereupon the probe 16a need not enter the mold to pass the energy through the mold.

Figure 7:
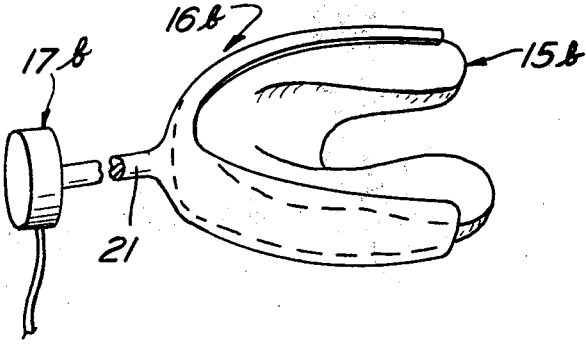
FIG. 7 is a top perspective view showing another slightly modified positioner, mold or tray of the present invention including a further modified activating means.

A further embodiment is shown in FIG. 7, wherein a mold 15b is fabricated of material permeable to radiant energy, such as material transparent to ultraviolet light. A radiant energy conductor 16b may assume a general U-shaped overall configuration for close circumposition about the mold 15b, and may be connected, as by a stem portion 21 to a radiant energy source 17b. Thus, radiant energy may be transmitted simultaneously through the entire mold 15b, or such lesser part thereof as desired, to activate the adhesive, as described hereinbefore, without physical penetration of the mold.

It is now seen that the present invention provides a uniquely improved method and apparatus for more quickly and easily applying orthodontic brackets to a patient's teeth, in accurately positioned relation, and which otherwise fully accomplishes its intended objects.

Although the present invention has been described in some detail by way of illustration and example for purposes of clarity of understanding, it is understood that certain changes and modifications may be made within the spirit of the invention.

What is claimed is:

1. In an orthodontic method, the steps which comprise: making a dental cast of the patient, selectively positioning and detachably applying brackets to the dental cast positioned as desired on the patient's teeth, applying a molding material into conforming engagement with the dental cast and brackets to define a mold which assumes the configuration of the dental cast and captures the brackets, removing the mold and captured brackets from the dental cast, applying said mold and brackets to the patient's teeth with selectively activatable adhesive interposed between the brackets and teeth, activating the adhesive by passing activating energy through the mold to secure the positioned brackets to the teeth, and removing the mold from the teeth while leaving the brackets secured.

2. The orthodontic method according to claim 1, further characterized in activating said adhesive by passing radiant energy through said mold.

3. The orthodontic method according to claim 2, further characterized in passing said radiant energy optically.

4. The orthodontic method according to claim 3, further characterized in passing said radiant energy through conductive paths in said mold directed at said adhesive.

5. The orthodontic method according to claim 1, further characterized in applying light activatable adhesive between said brackets and teeth, and passing light energy through light conductive means in said mold.

6. The orthodontic method according to claim 5, further characterized in passing ultraviolet light energy.

7. Orthodontic apparatus comprising, in combination, a dental cast of a patient, a plurality of brackets removably applied to the teeth of said dental cast at selected locations thereon, a positioner in conforming engagement with said dental cast teeth and applied brackets for removal together with said brackets from said teeth, said positioner with said brackets being conformably engageable with the patient's teeth to selectively locate the brackets in facing relation with the patient's teeth, energy activatable adhesive interposable between the brackets and patient's teeth for effecting securement therebetween, and selectively operable activating means penetrating through said positioner for selectively activating said adhesive, said activating means comprising energy conductive means in said positioner for conducting energy to the adhesive, whereby the positioner can be placed on the patient's teeth, the adhesive activated through the activating means thereby securing the brackets to the teeth and allowing the positioner to be removed leaving the brackets selectively located on the patient's teeth.

8. Apparatus according to claim 7, said adhesive being activatable by radiant energy, and said activating means comprising a radiant energy source, and radiant energy transmission means for delivering energy to said adhesive.

9. Orthodontic apparatus according to claim 8, said adhesive being light activatable, and said activating means comprising a light source, and a light conducting means communicating between said source and said adhesive for conducting light to the latter.

10. Orthodontic apparatus comprising, in combination, a dental cast of a patient, a plurality of brackets removably applied to the teeth of said dental cast at selected locations thereon, a positioner in conforming engagement with said dental cast teeth and applied brackets for removal together with said brackets from said teeth, said positioner with said brackets being conformably engageable with the patient's teeth to selectively locate the brackets in facing relation with the patient's teeth, selectively activatable adhesive interposable between the brackets and patient's teeth, for effecting securement therebetween, and selectively operable activating means penetrating through said positioner for selectively activating said adhesive, whereby the positioner can be placed on the patient's teeth, the adhesive activated through the activating means thereby securing the brackets to the teeth and allowing the positioner to be removed leaving the brackets selectively located on the patient's teeth, said adhesive being activatable by radiant energy, and said activating means comprising a radiant energy source, and radiant energy transmission means for delivering energy to said adhesive, said adhesive being light activatable, and said activating means comprising a light source, and a light conducting means communicating between said source and said adhesive for conducting light to the latter, said light conducting means comprising elongate optical elements embedded in said positioner.

11. Orthodontic apparatus according to claim 10, said light source being of ultraviolet light.

12. Orthodontic apparatus according to claim 9, said light conducting means comprising a probe insertable into said positioner for conducting light through the latter to a selected bracket and its associated adhesive.

13. Orthodontic apparatus according to claim 9, said positioner being transparent, and said light conductive means comprising an arcuate segment in conforming relation with said positioner.

* * * * *